(12) United States Patent  (10) Patent No.: US 7,611,486 B2
Jones et al.                (45) Date of Patent:     Nov. 3, 2009

(54) NEEDLE RETRACTION STRUCTURE

(75) Inventors: Scott Jones, University City, MO (US); George Clark, Lewis Center, OH (US)

(73) Assignee: Tyco Healthcare Group LP, Mansfield, MA (US)

( * ) Notice: Subject to any disclaimer, the term of this patent is extended or adjusted under 35 U.S.C. 154(b) by 370 days.

(21) Appl. No.: 11/525,377

(22) Filed: Sep. 22, 2006

(65) Prior Publication Data

US 2007/0066960 A1    Mar. 22, 2007

Related U.S. Application Data

(60) Provisional application No. 60/719,881, filed on Sep. 22, 2005.

(51) Int. Cl.
*A61M 5/00* (2006.01)
(52) U.S. Cl. ..................................... 604/110
(58) Field of Classification Search ........... 604/263, 604/192–198, 110, 158, 164, 168, 171, 111, 604/161, 162, 165, 191, 272
See application file for complete search history.

(56) References Cited

U.S. PATENT DOCUMENTS

| | | |
|---|---|---|
| 4,183,246 A | 1/1980 | Reynolds |
| 4,676,783 A | 6/1987 | Jagger et al. |
| 4,690,675 A | 9/1987 | Katz |
| 4,747,831 A | 5/1988 | Kulli |
| 4,781,692 A | 11/1988 | Jagger et al. |
| 4,813,426 A | 3/1989 | Haber et al. |
| 4,820,282 A | 4/1989 | Hogan |
| 4,900,307 A | 2/1990 | Kulli |
| 4,900,311 A | 2/1990 | Stern et al. |
| 4,973,316 A | 11/1990 | Dysarz |
| 4,994,034 A | 2/1991 | Botich et al. |
| 5,084,030 A | 1/1992 | Byrne et al. |
| 5,085,639 A | 2/1992 | Ryan |
| 5,088,982 A | 2/1992 | Ryan |
| 5,108,376 A | 4/1992 | Bonaldo |
| 5,114,410 A | 5/1992 | Caralt Batlle |
| 5,120,320 A | 6/1992 | Fayngold |
| 5,125,414 A | 6/1992 | Dysarz |
| 5,129,884 A | 7/1992 | Dysarz |
| 5,147,327 A | 9/1992 | Johnson |
| 5,176,655 A | 1/1993 | McCormick et al. |

(Continued)

FOREIGN PATENT DOCUMENTS

EP    1 221 305 B1    10/2005

(Continued)

OTHER PUBLICATIONS

International Search Report (Form PCT/ISA/210 (first & second sheet) (Apr. 2005) for International Appln. No. PCT/US06/37278, filed Sep. 22, 2006.

*Primary Examiner*—Manuel A Mendez

(57) ABSTRACT

A safety needle device is provided having any elongated housing and a needle assembly movable within the elongate housing. Retraction structure is provided to move the needle assembly from an extended position relative to the elongate housing to a retracted position within the elongate housing. A blocking member is provided to immobilize the retraction structure prior to use. The blocking member is insertable between the retraction structure and the associated elongate housing and/or the needle assembly.

16 Claims, 10 Drawing Sheets

U.S. PATENT DOCUMENTS

| | | | |
|---|---|---|---|
| 5,188,119 A | 2/1993 | Sunderland | |
| 5,188,599 A | 2/1993 | Botich et al. | |
| 5,192,275 A | 3/1993 | Burns | |
| 5,226,894 A | 7/1993 | Haber et al. | |
| 5,232,456 A | 8/1993 | Gonzalez | |
| 5,267,961 A | 12/1993 | Shaw | |
| 5,273,540 A | 12/1993 | Luther et al. | |
| 5,318,538 A | 6/1994 | Martin | |
| 5,330,438 A | 7/1994 | Gollobin et al. | |
| 5,338,303 A | 8/1994 | King et al. | |
| 5,376,075 A | 12/1994 | Haughton et al. | |
| 5,385,551 A | 1/1995 | Shaw | |
| 5,389,076 A | 2/1995 | Shaw | |
| 5,395,347 A | 3/1995 | Blecher et al. | |
| 5,407,431 A | 4/1995 | Botich et al. | |
| 5,409,461 A | 4/1995 | Steinman | |
| 5,423,758 A | 6/1995 | Shaw | |
| 5,501,675 A | 3/1996 | Erskine | |
| 5,538,508 A | 7/1996 | Steyn | |
| 5,549,571 A | 8/1996 | Sak | |
| 5,554,130 A | 9/1996 | McDonald et al. | |
| 5,562,629 A | 10/1996 | Haughton et al. | |
| 5,562,634 A * | 10/1996 | Flumene et al. | 604/171 |
| 5,573,510 A | 11/1996 | Isaacson | |
| 5,575,777 A | 11/1996 | Cover et al. | |
| 5,578,011 A | 11/1996 | Shaw | |
| 5,591,138 A | 1/1997 | Vaillancourt | |
| 5,632,733 A | 5/1997 | Shaw | |
| 5,676,658 A | 10/1997 | Erskine | |
| 5,695,475 A | 12/1997 | Best, Jr. et al. | |
| 5,746,215 A | 5/1998 | Manjarrez | |
| 5,779,679 A | 7/1998 | Shaw | |
| 5,810,775 A | 9/1998 | Shaw | |
| 5,928,199 A | 7/1999 | Nakagami | |
| 5,931,815 A | 8/1999 | Liu | |
| 5,951,525 A | 9/1999 | Thorne et al. | |
| 5,997,512 A | 12/1999 | Shaw | |
| 6,015,438 A | 1/2000 | Shaw | |
| 6,056,726 A | 5/2000 | Isaacson | |
| 6,077,244 A * | 6/2000 | Botich et al. | 604/110 |
| 6,080,137 A | 6/2000 | Pike | |
| 6,090,078 A | 7/2000 | Erskine | |
| 6,096,005 A | 8/2000 | Botich et al. | |
| 6,179,812 B1 | 1/2001 | Botich et al. | |
| 6,210,371 B1 | 4/2001 | Shaw | |
| 6,221,055 B1 | 4/2001 | Shaw et al. | |
| RE37,439 E | 11/2001 | Firth et al. | |
| 6,494,863 B1 | 12/2002 | Shaw et al. | |
| 6,524,276 B1 | 2/2003 | Halseth et al. | |
| 6,547,762 B1 | 4/2003 | Botich et al. | |
| 6,572,584 B1 | 6/2003 | Shaw et al. | |
| 6,582,402 B1 | 6/2003 | Erskine | |
| 6,620,136 B1 | 9/2003 | Pressly, Sr. et al. | |
| 6,641,555 B1 | 11/2003 | Botich et al. | |
| 6,673,047 B2 | 1/2004 | Crawford et al. | |
| 6,743,186 B2 | 6/2004 | Crawford et al. | |
| 6,773,419 B2 | 8/2004 | Crawford et al. | |
| 6,786,875 B2 | 9/2004 | Barker et al. | |
| 6,835,190 B2 | 12/2004 | Nguyen | |
| 6,860,872 B2 | 3/2005 | Teichert | |
| 6,905,478 B2 | 6/2005 | Ingram et al. | |
| 6,942,652 B1 * | 9/2005 | Pressly et al. | 604/508 |
| 6,945,960 B2 | 9/2005 | Barker et al. | |
| 6,972,002 B2 | 12/2005 | Thorne | |
| 6,976,976 B2 | 12/2005 | Doyle | |
| 7,037,292 B2 | 5/2006 | Carlyon et al. | |
| 7,422,572 B2 * | 9/2008 | Popov et al. | 604/198 |
| 2003/0040717 A1 | 2/2003 | Saulenas et al. | |
| 2003/0078540 A1 | 4/2003 | Saulenas et al. | |
| 2003/0093035 A1 | 5/2003 | Mohammed | |
| 2003/0199830 A1 | 10/2003 | Nguyen | |
| 2003/0220619 A1 | 11/2003 | Polidoro et al. | |
| 2004/0193110 A1 | 9/2004 | Giambattista et al. | |
| 2004/0267200 A1 | 12/2004 | Carlyon et al. | |

FOREIGN PATENT DOCUMENTS

| | | |
|---|---|---|
| WO | WO 00/47256 | 8/2000 |

* cited by examiner

NEEDLE RETRACTION STRUCTURE

CROSS REFERENCE TO RELATED APPLICATION

This patent application claims priority to U.S. Provisional Application Ser. No. 60/719,881, filed Sep. 22, 2005, which is incorporated herein in its entirety by reference.

BACKGROUND

1. Technical Field

The present disclosure relates to a safety needle for use in various intravenous procedures. More particularly, the present disclosure relates to a safety needle having retraction structure and a safety sheath for preventing inadvertent actuation of the retraction structure.

2. Background of Related Art

Hypodermic needles are used for venous access in a variety of medical procedures requiring fluid sampling, percutaneous medication injection, or other delivery to or withdrawal of fluid from a patient. Various intravenous needle assemblies are known which can generally include blood collection needles, infusion needles, hemodialysis needles, needles associated with blood collection bags, etc. Problems associated with the use of intravenous needles may include needlestick injury, stabilization of the needle relative to the implant, and ease of insertion and withdrawal of the needle from the patient.

Some of the health risks associated with hazardous needle exposure include HIV, hepatitis, and other blood-borne pathogens. Medical professionals are in danger of contracting such blood-borne pathogens from infected patients by inadvertent needle sticks from the contaminated needle employed during medical, dental, laboratory, etc. procedures.

Various protective devices, or sheaths have been used to shield the sharp tips of the needles in order to alleviate the danger of needlestick injury to the user. Additionally, many needle devices include the provision of an automatic retraction system to shield the needle within a housing associated with the needle assembly after use. However, these retraction mechanisms may inadvertently be activated prior to use, for example, during shipping or unpackaging thereby rendering the device unsuitable for use. Examples of devices including spring-loaded retraction mechanisms which have no provision for preventing inadvertent, premature retraction include U.S. Pat. No. 5,423,758 to Shaw, U.S. Pat. No. 5,779,679 to Shaw, U.S. Pat. No. 6,096,005 to Botich, U.S. Pat. No. 6,179,812 B1 to Botich and U.S. Pat. No. 6,210,371 B1 to Shaw.

It would be desirable to provide a safety needle device incorporating a blocking member to prevent inadvertent actuation of the retraction mechanism during shipping and unpackaging. It would also be desirable to incorporate the blocking mechanism with a sheath assembly in order to prevent actuation of the retraction mechanism until such time as the sheath is removed immediately prior to use.

SUMMARY

There is disclosed a safety needle device for use in various intravenous procedures. The safety needle device generally includes an elongate housing and a needle assembly movably mounted within the elongate housing. The safety needle device further includes an actuator associated with the needle assembly which is movably mounted within the elongate housing from a first position preventing movement of the needle assembly into the elongate housing to a second position allowing movement of the needle assembly into the elongate housing. The safety needle device additionally includes a blocking member removably positioned relative to the actuator to prevent movement of the actuator from the first position to the second position. The blocking member is positioned between the actuator and the needle assembly. In one embodiment, the blocking member is a safety sheath covering the needle of the needle assembly. In one embodiment, the actuator includes a release button which is configured to engage a distal end of the elongate housing. A blocking member is positioned between the release button and the needle assembly.

In one embodiment the actuator is part of a retraction mechanism which includes a spring affixed to the actuator and the elongate housing to bias the needle assembly proximally within the elongate housing.

In one embodiment the needle assembly includes an elongate needle and a tube extending proximally from the elongate needle, wherein the blocking member is removably positioned between the release button and the tube.

There is also disclosed a safety needle device having an elongate housing and a needle assembly movably mounted within the elongate housing. A retraction mechanism mounted within the elongate housing and is operatively associated with the needle assembly to move the needle assembly from an extended position relative to the elongate housing to a retracted position within the elongate housing. A blocking member is removably positioned on the needle assembly such that the retraction mechanism is disabled. The retraction mechanism includes an actuator and a tension spring positioned between the actuator and the elongate housing. The actuator includes a release button engageable with the elongate housing. The blocking member is removably positioned between the needle assembly and the release button. The release button is movable from a first position engaged with the elongate housing to a second position disengaged from the elongate housing. The needle assembly includes a needle and a tube extending proximally from the needle. In this embodiment, the actuator is affixed to the tube.

In one embodiment, the retraction mechanism includes a spring positioned within a first chamber of the elongate member and the needle assembly is positioned in a second chamber of the elongate member. The first and second chambers have parallel, offset axes such that the spring and the needle assembly are positioned parallel to each other within the elongate housing.

There is also disclosed a method of preventing inadvertent retraction of a spring biased safety needle prior to use by providing a safety needle having an elongate housing and a needle assembly movably mounted within the elongate housing. An actuator associated with the needle assembly is movable from a first position preventing movement of the needle assembly to a second position allowing movement of the needle assembly. A blocking member is removably provided on the safety needle and positionable between the actuator and the needle assembly. The method includes inserting the blocking member between the actuator and the needle assembly to prevent movement of the actuator.

In one embodiment, the actuator includes a release button and the blocking member is inserted between the release button and a needle assembly to prevent movement of the release button.

In one embodiment, the needle assembly includes a tube and a blocking member is inserted between the release button and the tube.

In one embodiment, the needle assembly also includes a needle extending distally from the tube and the blocking member is a safety sheath which is inserted over the needle and the tube such that a proximal end of the blocking member is positioned between the release button and the tube to prevent movement of the release button.

DESCRIPTION OF THE DRAWINGS

Embodiments of the presently disclosed safety needle and needle retraction structure are disclosed herein with reference to the drawings, wherein.

DETAILED DESCRIPTION OF EMBODIMENTS

An embodiment of the presently disclosed safety needle and retraction structure will now be described in detail with reference to the drawings wherein like numerals designate identical or corresponding elements in each of the several views. As is common in the art, the term 'proximal" refers to a location or position on a device closer to the user or operator, i.e. surgeon or physician, while the term "distal" refers to a location or position on a device further away from the user.

Figure 1:
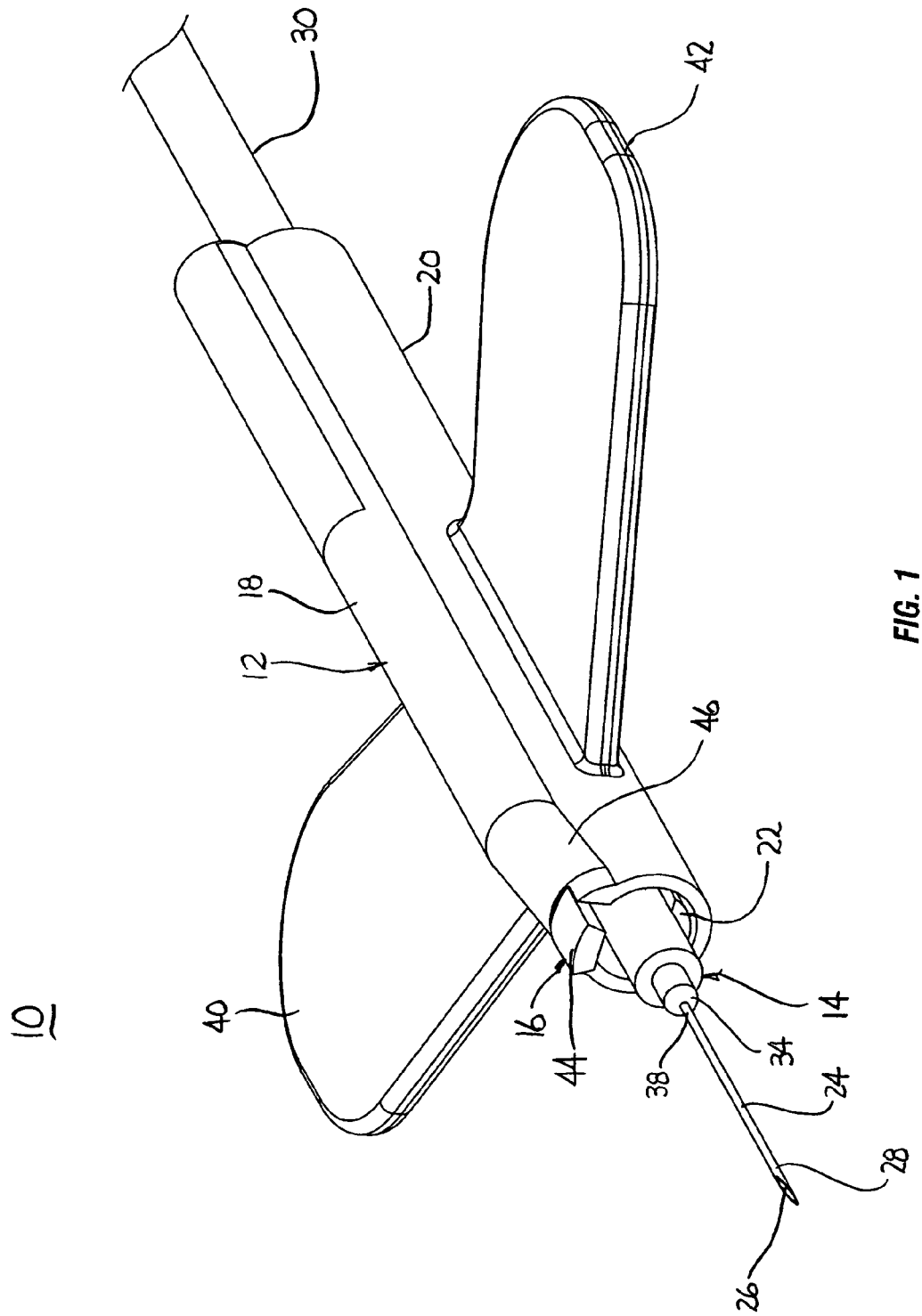
FIG. 1 is a perspective view of one embodiment of the presently disclosed safety needle.

FIG. 1 illustrates one embodiment of the presently disclosed safety needle, shown generally as 10, suitable for use in a variety of surgical procedures requiring the infusion, injection or withdrawal of fluids from the body of a patient. Safety needle 10 includes an elongate housing 12 having a needle assembly 14 movably mounted within elongate housing 12. An actuator 16 is associated with needle assembly 14 and is also movably mounted within elongate housing 12.

Referring also to FIGS. 2-6, elongate housing 12 includes an upper chamber 18 containing a portion of a retraction mechanism, described in more detail hereinbelow, and a lower chamber 20 having a through bore 22 for receipt of needle assembly 14.

Needle assembly 14 includes an elongate hollow needle 24 having a tissue penetrating tip 26 at a distal end 28 of needle 24. Needle 24 is of the type typically used during intravenous procedures to insert and withdraw fluids from the body. Needle assembly 14 further includes tubing 30 having a first end 36 and a second end and defining a throughbore 32 (FIG. 5) which is in fluid communication with needle 24. A connector 34 (FIG. 5) is provided to engage a first end 36 of tubing 30 and attach a proximal end 38 of needle 24 to tubing 30.

Elongate housing 12 further includes a first stabilizing wing 40 and a second stabilizing wing 42 to facilitate insertion of needle assembly 14 into the body of a patient and to stabilize elongate housing 12 on a patient during the insertion or withdrawal of fluids. Stabilizing wings 40 and 42 may be either rigid to maximize the stability of elongate housing 12 relative to a patient or, alternatively, may be relatively flexible to allow bending and grasping by the user to aid in insertion of needle assembly 14 into the body of a patient.

Figure 5:
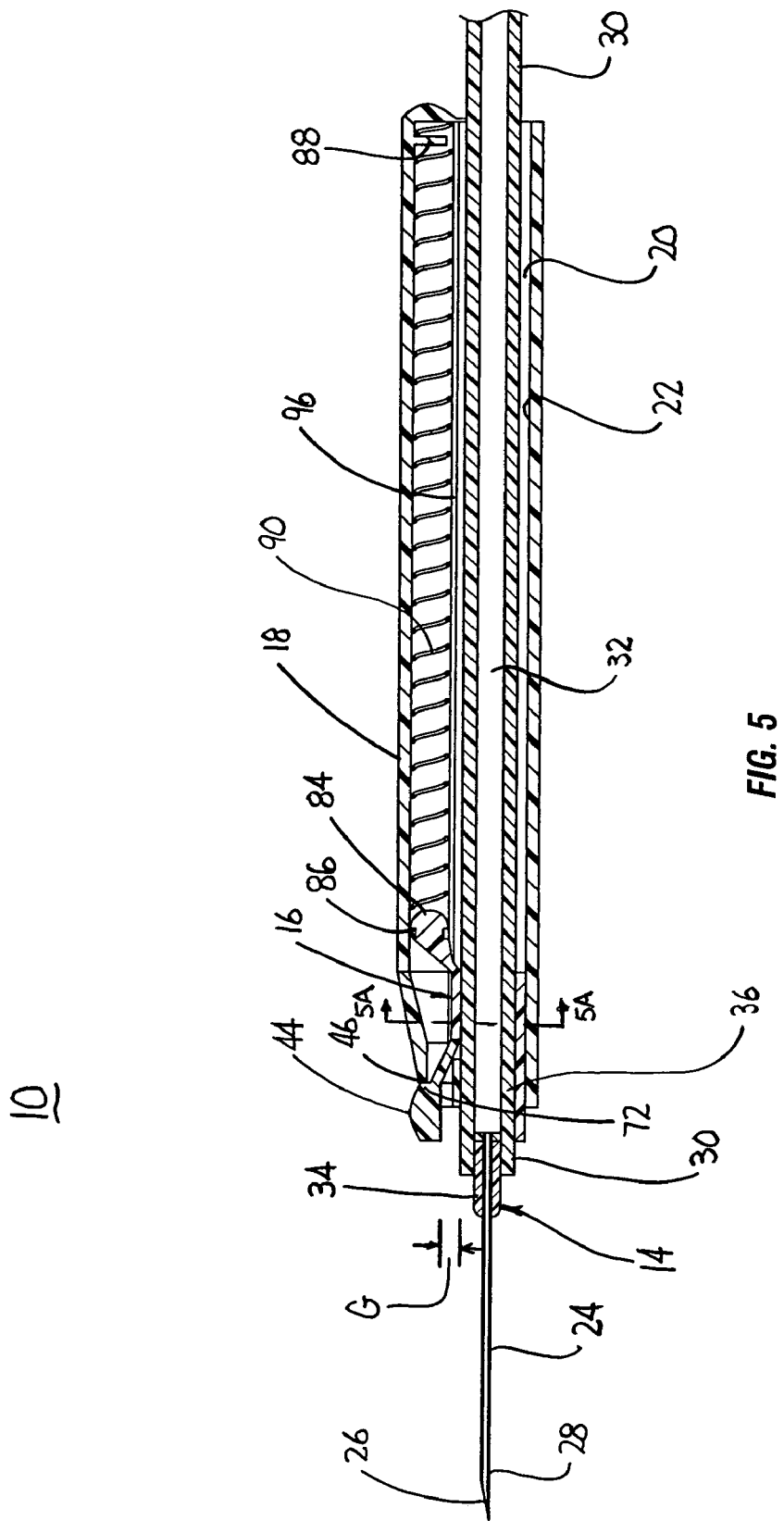
FIG. 5 is a side view, shown in section, of the embodiment of FIG. 1 with the needle in the extended position.
Figure 5A:
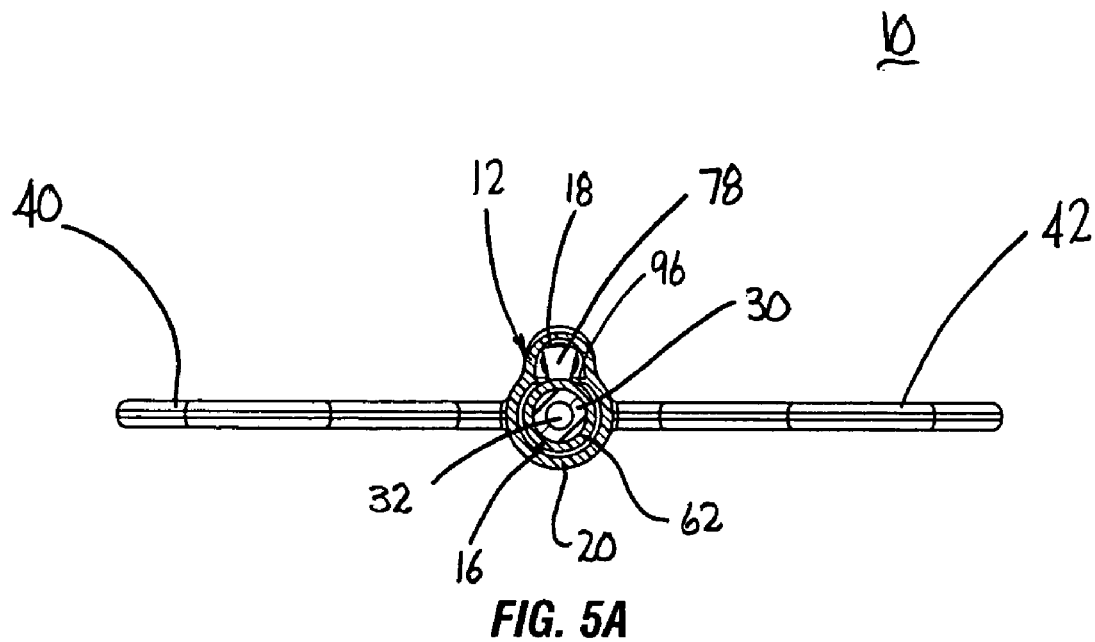
FIG. 5A is a cross-sectional view taken along section lines 5A-5A of FIG. 5.

As shown, actuator 16 includes a release button 44 which extends from a distal end 46 of upper chamber 18 (See FIG. 5). Release button 44 cooperates with a retraction structure in upper chamber 18 in a manner described in more detail hereinbelow to retract needle assembly 16 within elongate housing 12.

Figure 2:
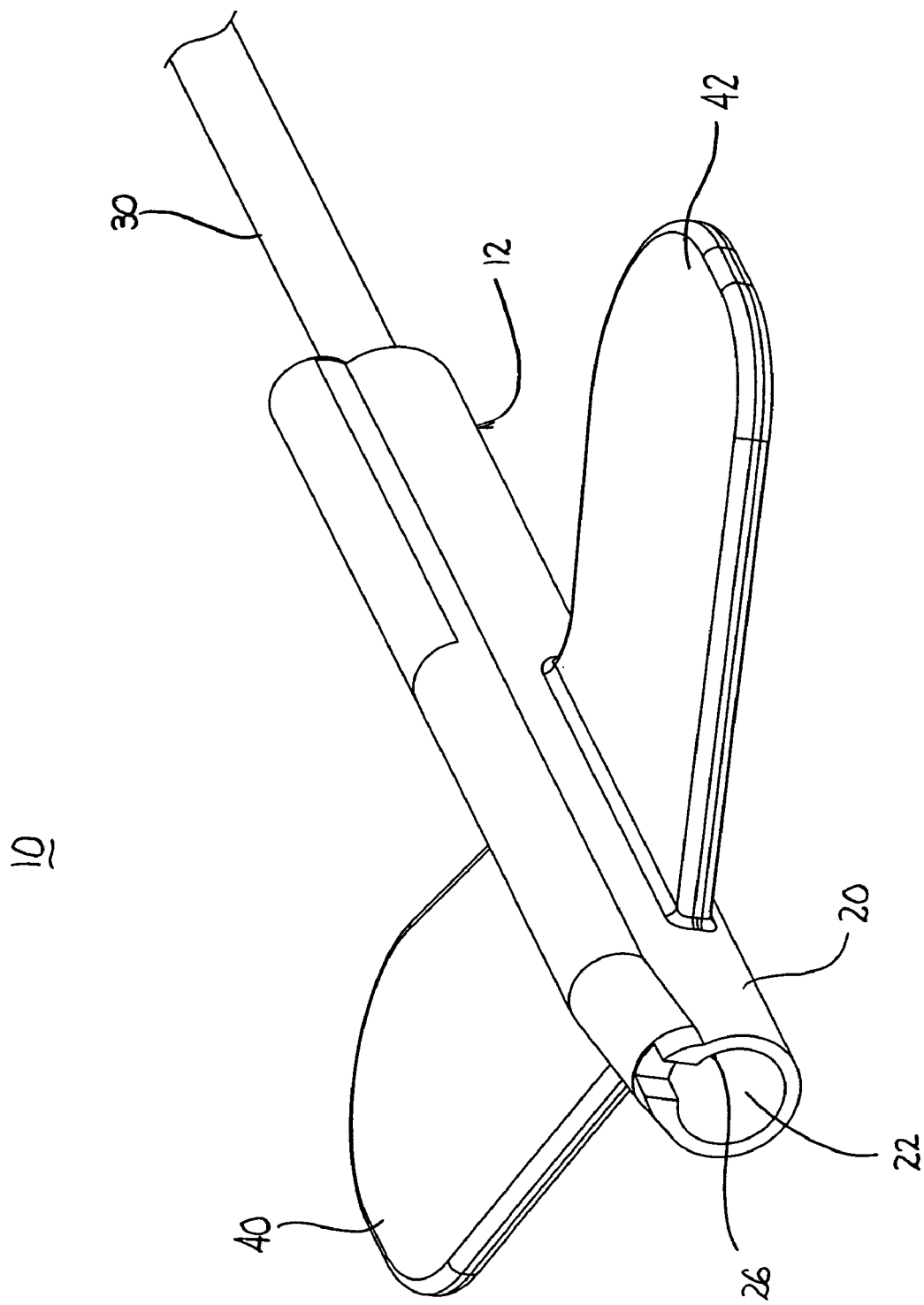
FIG. 2 is a perspective view of the safety needle of FIG. 1 with the needle retracted.

As best shown in FIG. 2, in the retracted position, needle assembly 14, and specifically tissue penetrating tip 26 of needle 24, is completely retained within a distal end 48 of through bore 22 in lower chamber 20. In the retracted position, the operator is completely protected from needlestick injury by tissue penetrating tip 26 of needle 24.

Figure 3:
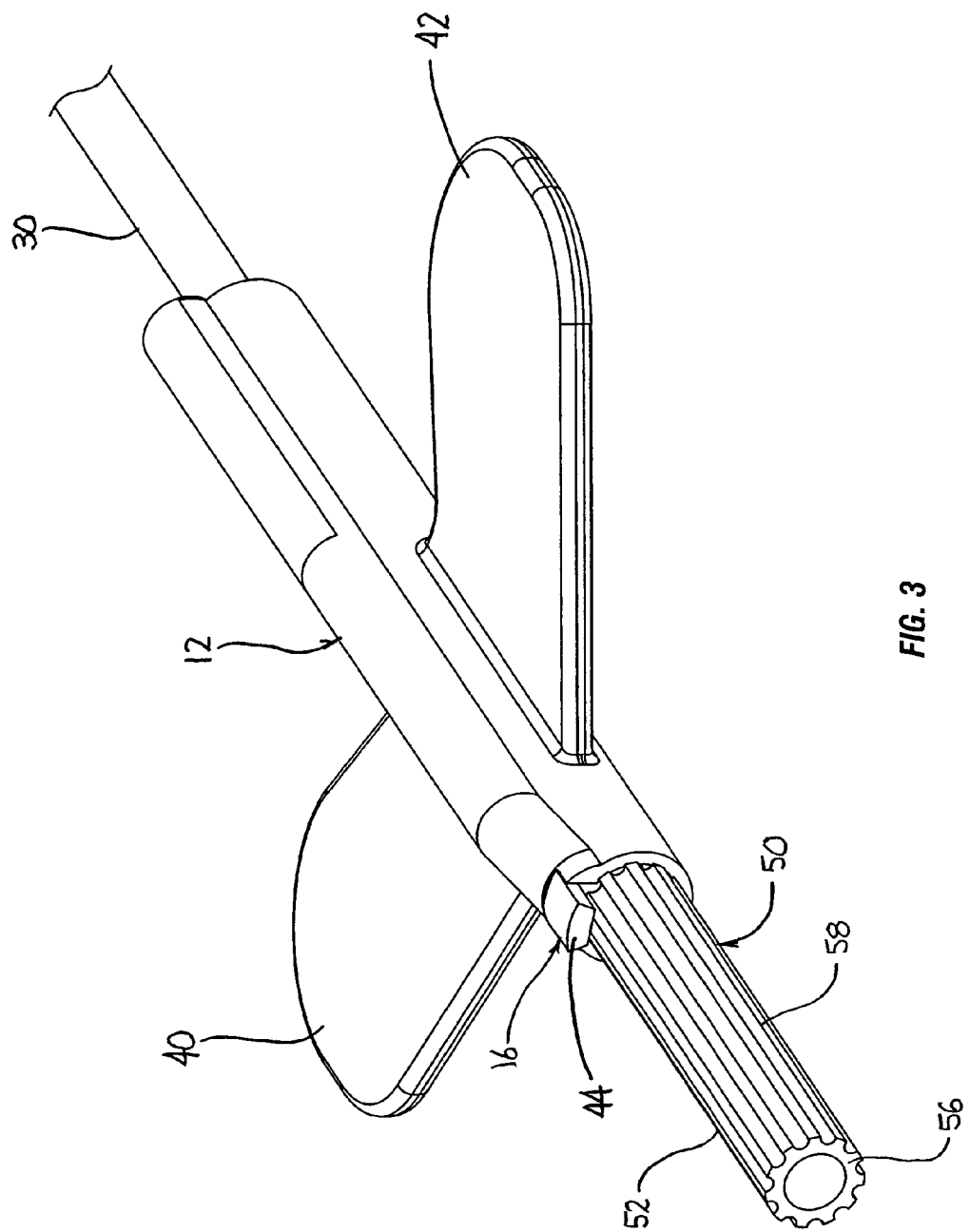
FIG. 3 is a perspective view of the safety needle of FIG. 1 including a safety sheath.

Turning now to FIG. 3, safety needle 10 is provided with a novel blocking structure or member 50 which prevents operation of actuator 16, and thus inadvertent retraction of needle assembly 14, until blocking member 50 has been removed from needle 24. This is particularly useful to prevent inadvertent retraction of needle assembly 14 during packaging and transportation of safety needle 10. Specifically, in this embodiment, blocking member 50 is a safety sheath 52 which is configured to cover needle 24 to prevent needlestick injury to the user prior to the removal of safety sheath 52. In particular, when safety sheath 52 is positioned over needle 24, a proximal end 54 of safety sheath 52 is positioned between release button 44 and needle assembly 14 preventing movement of release button 44 in a direction to effect release of actuator 16 and thus preventing actuation of actuator 16.

Safety sheath 52 is formed of a sufficient length that, with needle assembly 14 in the extended position, a distal end 56 of safety sheath 52 covers and extends beyond tissue penetrating tip 26 of needle 24. An outer surface 58 of safety sheath 52 is longitudinally ridged to facilitate grasping by the user.

Figure 2A:
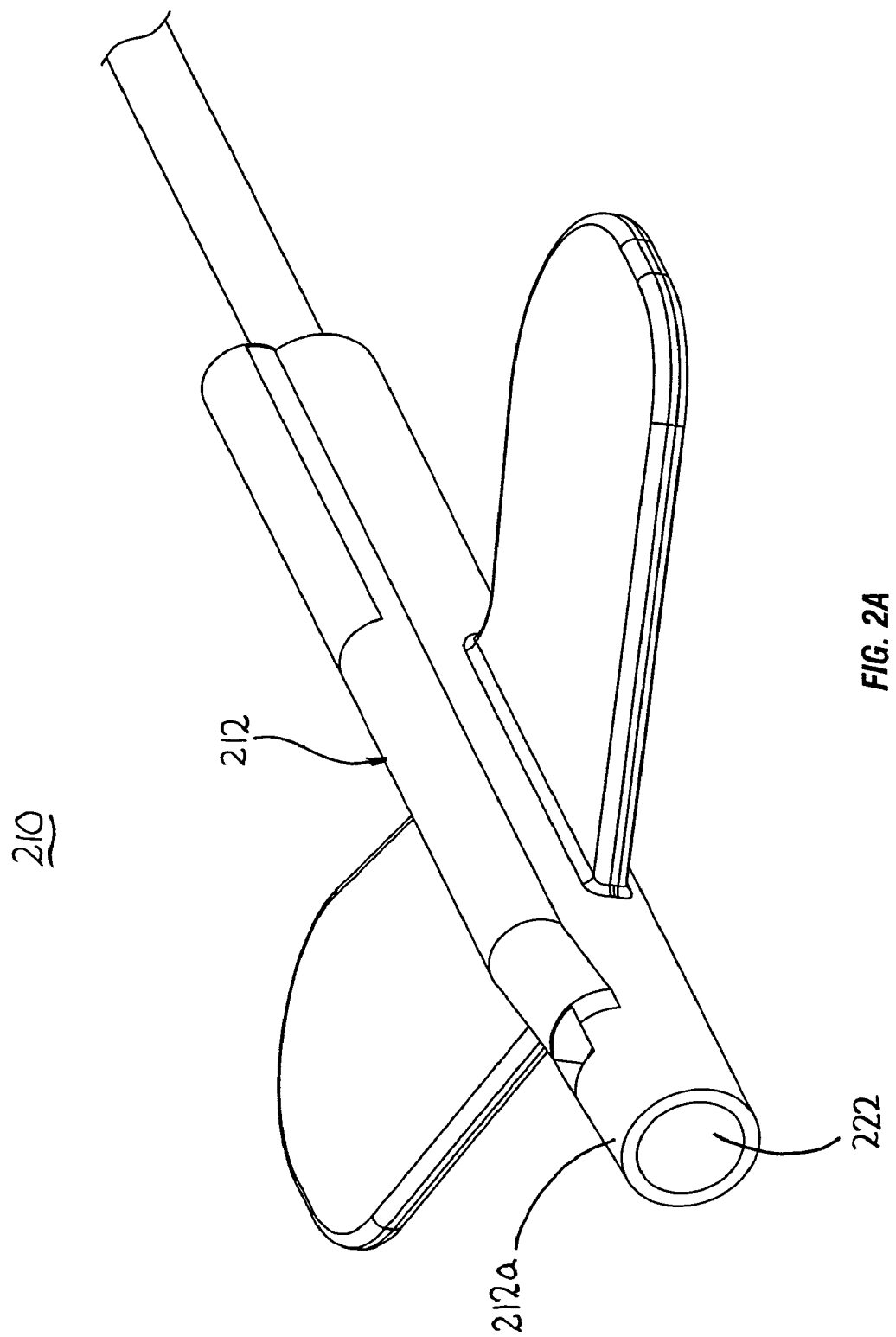
FIG. 2A is a perspective view of another embodiment of the presently disclosed safety needle with the needle in the retracted position.
Figure 3A:
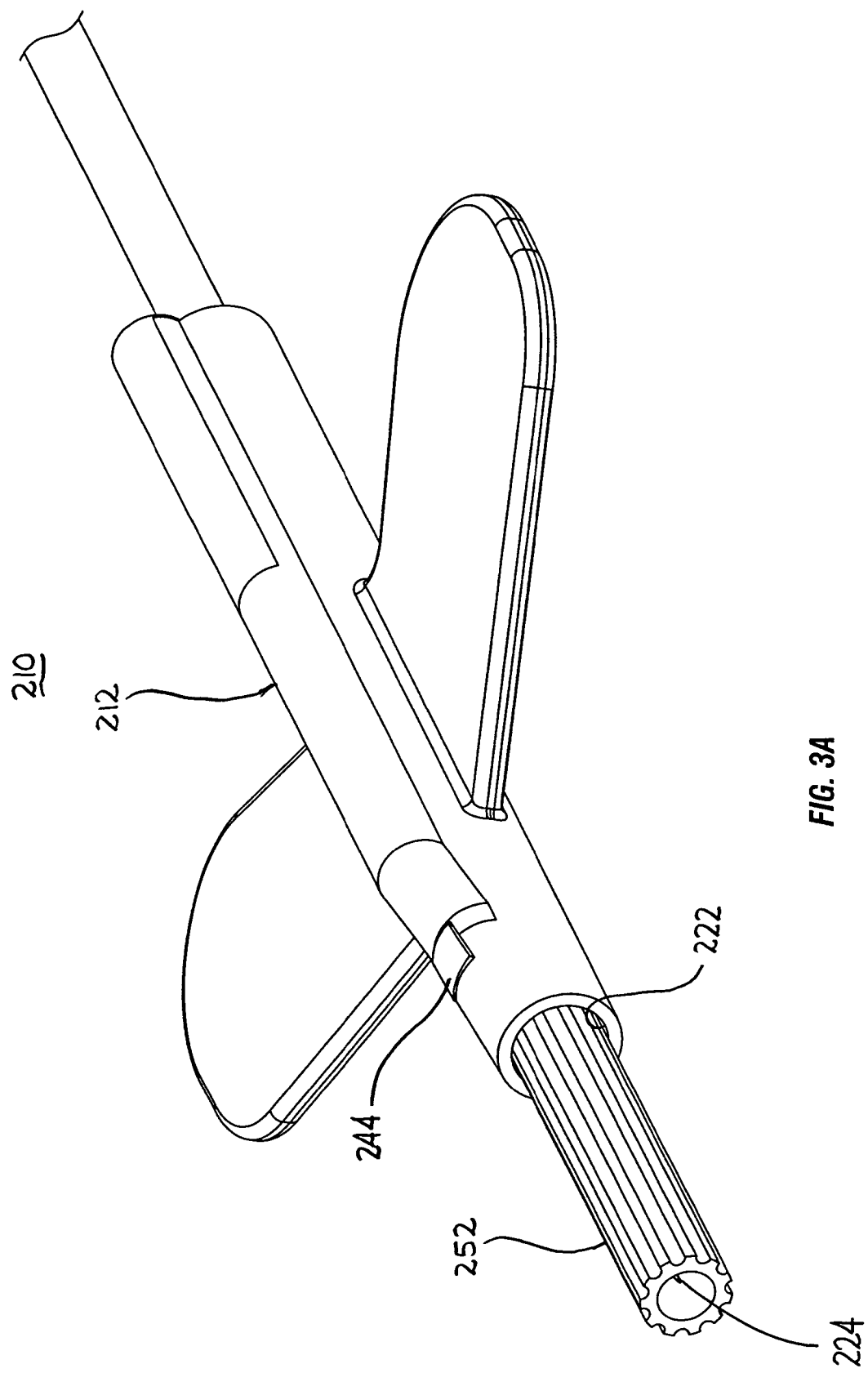
FIG. 3A is a perspective view of the safety needle shown in FIG. 2A with a safety sheath positioned over an extended needle.

FIGS. 2A and 3A illustrate an alternate embodiment of the presently disclosed safety needle shown generally as 210. Safety needle 210 is substantially similar to safety needle 10 with the exception that housing 212 includes a forwardmost portion 212a which extends forwardly beyond release button 244 (FIG. 3A). By positioning housing 212 distally of release button 244, distalmost portion 212a of housing 212 protects a clinician's fingers from engaging needle 224 if the clinicians fingers slip off of release button 244. As shown in FIG. 3A, distalmost portion 212a defines a throughbore 222 which is dimensioned to receive sheath 252 such that sheath 252 prevents actuation of release button 244 until sheath 252 is removed from safety needle 210.

Figure 4:
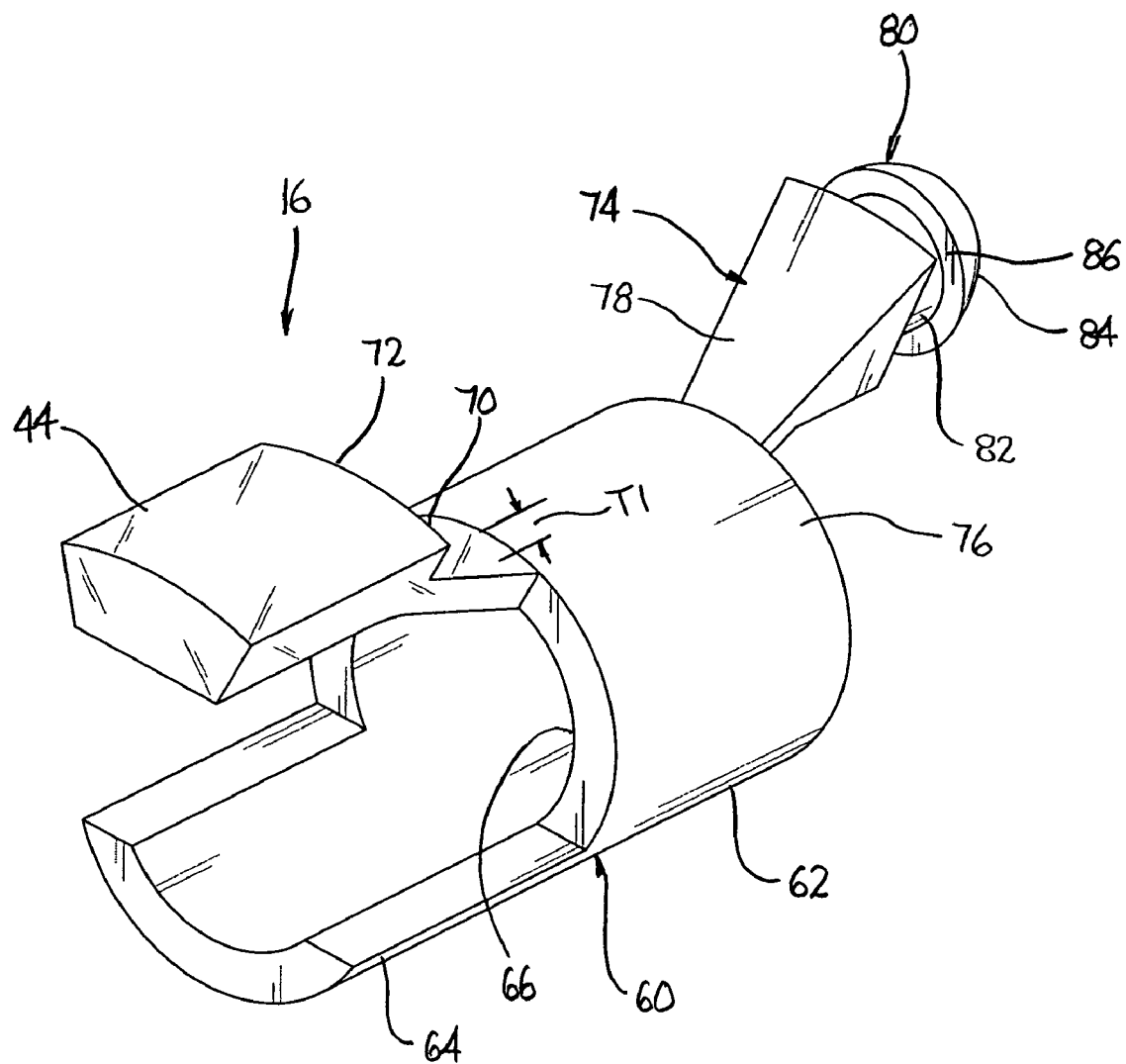
FIG. 4 is a perspective view of the actuator of the embodiment of FIG. 1.

Referring to FIGS. 4 and 5, actuator 16 is provided to retract needle assembly within lower chamber 20 of elongate housing 12. Actuator 16 includes an actuator barrel 60 which has a full diameter proximal section 62 and a partial diameter distal section 64. Proximal section 62 includes a through bore 66 for receipt of needle assembly 14. Actuator barrel 60 is configured and dimensioned to receive and securely engage needle assembly 14 to effect withdrawal of needle assembly 14 into elongate housing 12 in response to actuation of release button 44. In one embodiment, an inner surface 66 of proximal section 62 engages needle assembly 14 in a friction fit fashion. Alternately, proximal section 62 of actuator 16 may be permanently attached to needle assembly 14 by various means, such as, for example, thermal welding, gluing, etc., or monolithically or integrally formed therewith. Distal section 64 serves to support needle assembly 14 and prevents actuator 16 from flexing or twisting within lower chamber 20 as actuator 16 and needle assembly 14 are moved therein.

As discussed hereinabove, release button 44 is provided to disengage actuator 16 from upper chamber 18 of elongate housing 12 and allow retraction of needle assembly 14 within elongate housing 12. Release button 44 can be formed of a transparent material to facilitate visualization of the flow of fluid through needle assembly 14, i.e., "flashback". Release button 44 is mounted on or formed integrally with a flexible lever 70 which is attached to proximal section 62 (See FIG. 4). A proximal edge 72 of button 44 is configured to engage distal end 46 of upper chamber 18 to restrain needle assembly 14 against retraction into housing 12. Depression of button 44 against the bias of flexible lever 70 disengages button 44, i.e. proximal edge or stop surface 72, from distal end 46 of upper chamber 18. It should be noted that the thickness Ti of proximal edge 72 is such that proximal edge 72 cannot be disengaged from distal end 46 of upper chamber 18 when blocking member 50, e.g., safety sheath 52, is positioned between release button 44 and needle assembly 14.

In order to retract needle assembly 14 within elongate housing 12, actuator 16 is provided with a spring mount 74 extending proximally from proximal end 76 of proximal section 62. Spring mount 74 is configured to engage a retraction spring 90 positioned within upper chamber 18 (FIG. 5). In one embodiment, retraction spring 90 is a coil spring which is in tension. Spring mount 74 includes an arm 78 terminating in a button 80. Button 80 is configured to engage a distal end of the spring. Specifically, button 80 includes a shaft 82 extending proximally from arm 78 and a cap 84 extending proximally from shaft 82. Cap 84 has a diameter greater than the diameter of shaft 82 such that a proximal edge 86 of cap 84 secures a distal coil of spring 90 within upper chamber 18.

Referring to FIG. 5, upper chamber 18 is provided with a proximal spring mount 88 for engaging a proximal coil of retraction spring 90. As discussed hereinabove, a retraction or tension spring 90 is positioned within upper chamber 18. Tension spring 90 is configured to retract needle assembly 14 within housing 12 in response to actuation of actuator 16. A distal coil of tension spring 90 engages button 80 of actuator 16. Specifically, a distal most coil of tension spring 90 is retained against proximal edge 86 of cap 84. Notably, by positioning tension spring 90 in upper chamber 18, tension spring 90 does not surround needle assembly 14 and extends along a parallel axis offset from the longitudinal axis of needle assembly 14. This allows needle assembly 14, and in particular needle 24, to have a relatively low profile to the underside of elongate housing 12. This enables safety needle 10 to lie relatively flush to the arm of the patient and have a very low angle of attack as needle 24 is inserted into the arm of the patient. This also greatly facilitates the ability to stabilize safety needle 10 against the arm of the patient.

As discussed hereinabove, proximal end 54 of safety sheath 52 (FIG. 3) is retained within a gap "G" (FIG. 5) defined between release button 44 and needle assembly 14. Specifically, gap G is defined by the space between release button 44 and an outer surface of tubing 30. When safety sheath 52 is positioned within gap G, release button 44 is prevented from being depressed. Similarly, when safety sheath 52 is removed from needle assembly 14, release button 44 is free to be depressed to allow spring 90 to retract actuator 16 and thus needle assembly 14 within elongate housing 12.

As shown in FIG. 5, when proximal edge 72 of release button 44 is engaged with distal end 46 of upper chamber 18 spring 90 is in a tension urging needle assembly 14 to its retracted position.

Figure 6A:
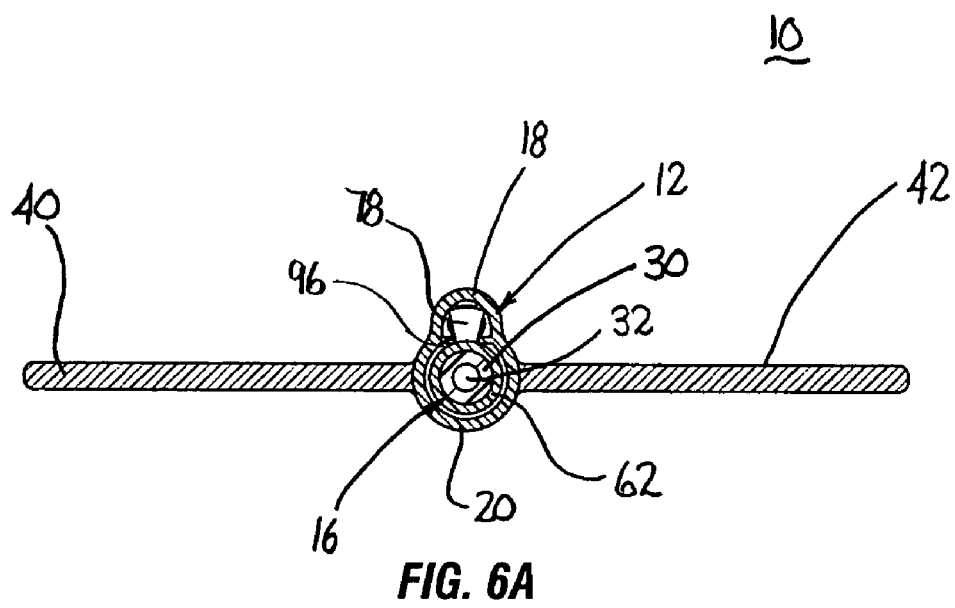
FIG. 6A is a cross-sectional view taken along section lines 6A-6A of FIG. 6.
Figure 6:
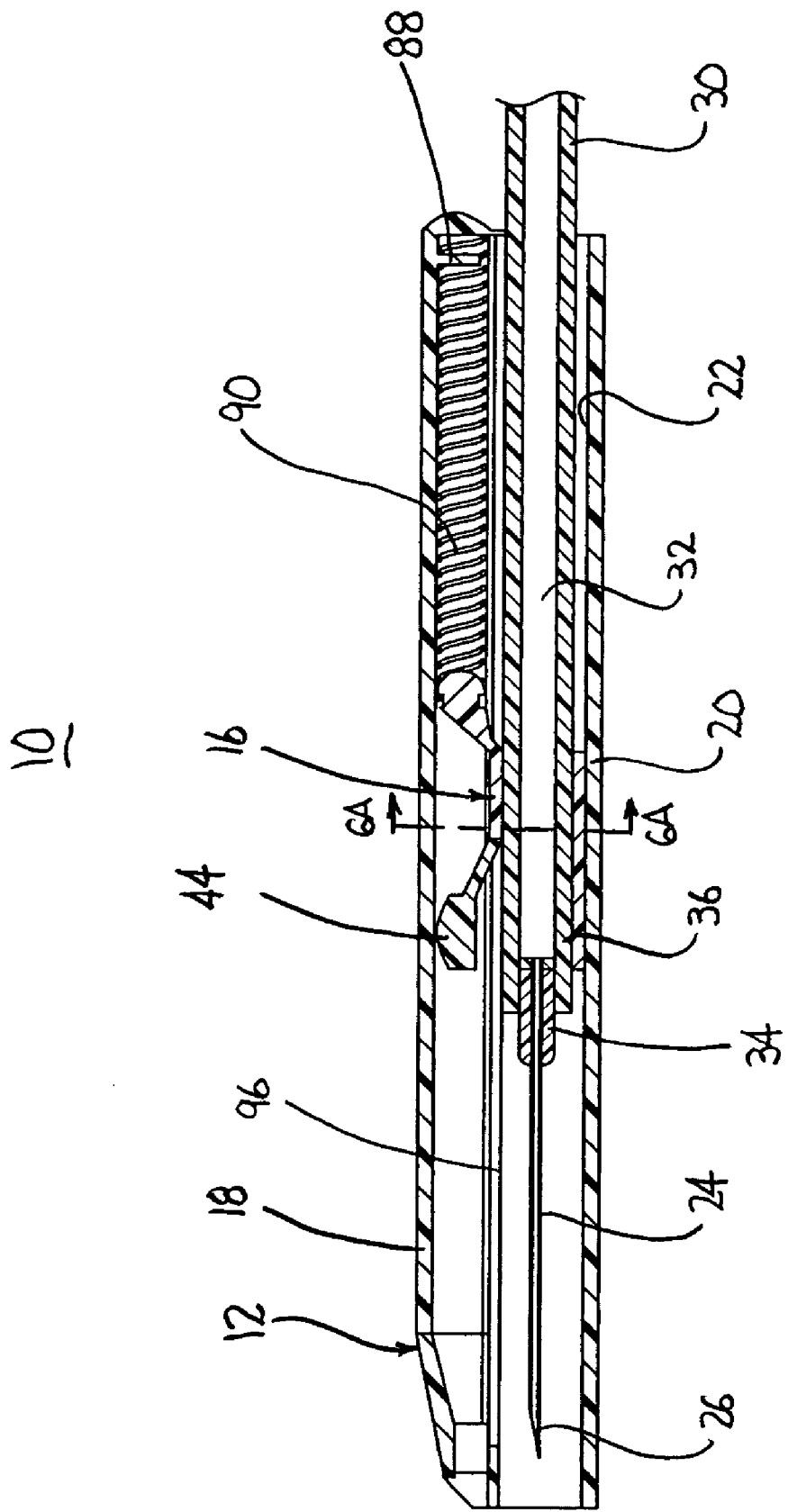
FIG. 6 is a side view, shown in section, of the embodiment of FIG. 1 with the needle in the retracted position.
Figure 7:
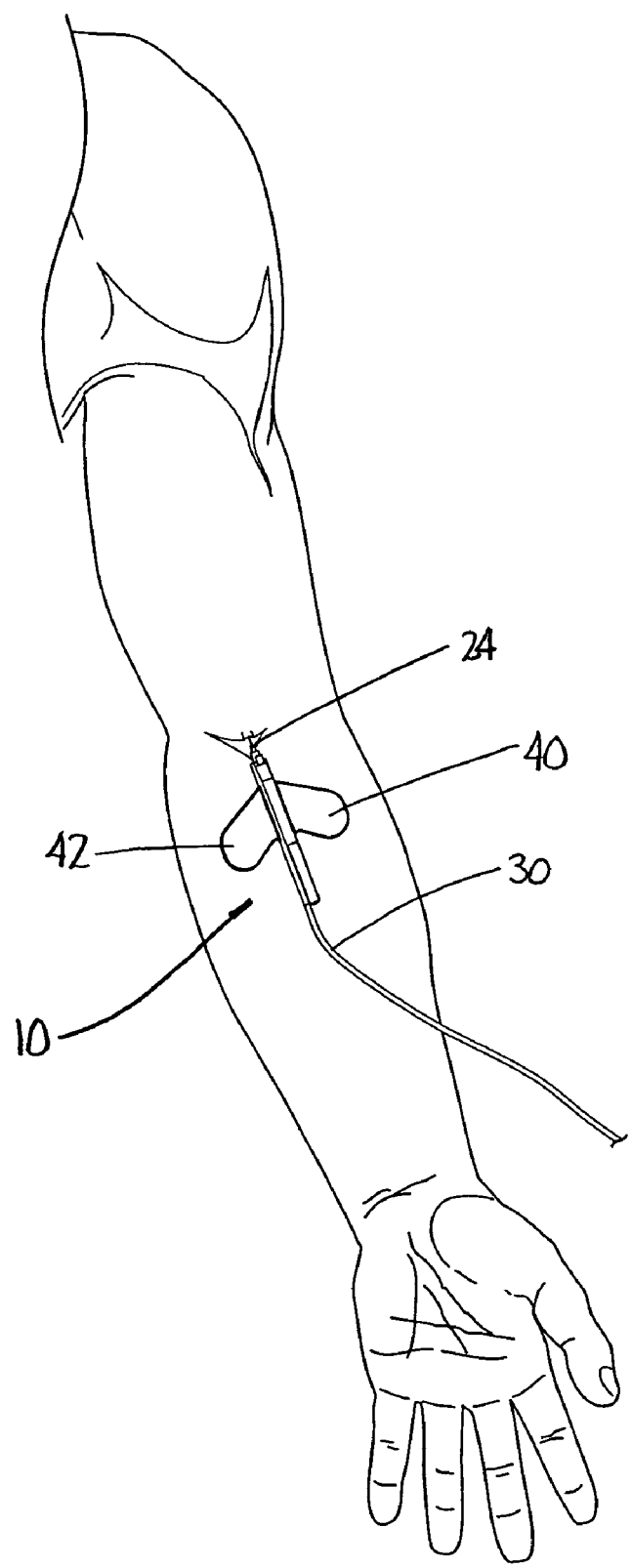
FIG. 7 is a perspective view of the safety needle of the embodiment of FIG. 1 inserted into a patient.

Referring now to FIGS. 3, 5 and 6, the operation of safety needle 10 will now be described. Referring initially to FIG. 3, safety needle 10 is supplied with safety sheath 52 positioned over needle assembly 14 and blocking release button 44 from actuation. Safety sheath 52 prevents inadvertent actuation of release button 44 during handling of the packaging or removal of needle assembly 14 from packaging and prior to use on a patient. When safety needle is ready to be used, safety sheath 52 is removed from needle assembly 14 to expose needle 24. As noted above, stabilizing wings 40 and 42 may be pinched or otherwise to held to facilitate insertion of tissue penetrating needle tip 26 into the body of a patient (FIG. 7).

Once needle tip 26 has been inserted into the body of a patient, the proper flow of fluid through needle assembly 14 can be viewed through release button 44 which, as noted above, is transparent to act as a flashback viewer. It is noted that all or a portion of needle 24, connector 34 and/or tubing 30 may also be transparent to facilitate viewing of the flow of fluid through needle assembly 14. After the surgical procedure has been completed, in conjunction with, or subsequent to, the removal of needle 24 from the body of a patient, release button 44 can be depressed against the bias of flexible lever 70 to disengage proximal edge 72 from distal end 46 of upper chamber 18. Once release button 44 has been disengaged from upper chamber 18, retraction spring 90 draws actuator 16, and thus needle assembly 14 attached thereto, proximally within elongate housing 12. It should be noted that a longitudinal slot 96 (FIGS. 5-6A) is provided between upper chamber 18 and lower chamber 20 to allow free movement of actuator 16 through elongate housing 12.

As best shown in FIG. 6, after retraction of needle assembly 14, tissue penetrating tip 26 of needle 24 is safely contained within lower chamber 20 of elongate housing 12 thereby preventing any needlestick injury to the user. Furthermore, actuator 16 is entirely contained within elongate housing 12 thereby preventing any possibility of needle 24 from being re-extended from within elongate housing 12.

It will be understood that various modifications may be made to the embodiments disclosed herein. For example, the actuator may include alternative structure for engaging the elongate housing such as, for example, pivotal arms, latches etc. Further, the blocking member need not be restricted to a safety sheath but can include other separate components insertable between retraction structure and an associated housing or support member, such as for example a key, a removable lever, etc. Additionally, the disclosed retraction structure is not limited to those instances where the needle assembly and retraction spring are off axis but may include those instances where in the needle assembly and associated retraction structure are coaxial. Therefore, the above description should not be construed as limiting, but merely as exemplifications of particular embodiments. Those skilled in the art will envision other modifications within the scope and spirit of the claims appended hereto.

The invention claimed is:
1. A safety needle device comprising:
an elongate housing;
a needle assembly movably mounted from an advanced position to a retracted position located within the elongate housing;

a retraction spring positioned in the housing to urge the needle assembly towards the retracted position;

an actuator secured to the needle assembly and movably mounted from a first position preventing movement of the needle assembly from the advanced position to the retracted position to a second position allowing movement of the needle assembly from the advanced position to the retracted position; and a blocking member removably positioned relative to the actuator to prevent movement of the actuator from the first position to the second position, wherein the actuator includes a release button which is positioned to engage a distal portion of the elongate housing when the actuator is in its first position to retain the needle assembly in the advanced position, the release button being positioned to slide within the elongate housing when the actuator is moved to its second position to permit movement of the needle assembly towards the retracted position, the blocking member being positioned between the needle assembly and the release button.

2. The safety needle device as recited in claim 1, wherein the blocking member is a safety sheath positioned about a needle of the needle assembly.

3. The safety needle device as recited in claim 1, wherein the spring is affixed to the elongate housing to bias the needle assembly proximally within the elongate housing.

4. The safety needle device as recited in claim 1, wherein the needle assembly includes an elongate needle and a tube extending from the elongate needle.

5. A safety needle device comprising:

an elongate housing;

a needle assembly movably mounted from an advanced position to a retracted position located within the elongate housing;

a retraction spring positioned in the housing to urge the needle assembly towards the retracted position;

a retraction mechanism operatively associated with the needle assembly to move the needle assembly from the advanced position to the retracted position within the elongate housing, the retraction mechanism including an actuator secured to the needle assembly and movably mounted from a first position preventing movement of the needle assembly from the advanced position to the retracted position to a second position allowing movement of the needle assembly from the advanced position to the retracted position; and a blocking member removably positionable on the needle assembly such that the retraction mechanism is disabled when the blocking member is positioned on the needle assembly, wherein the actuator includes a release button which is positioned to engage a distal portion of the elongate housing when the actuator is in its first position to retain the needle assembly in the advanced position, the release button being positioned to slide within the elongate housing when the actuator is moved to its second position to permit movement of the needle assembly towards the retracted position, the blocking member being positioned between the needle assembly and the release button.

6. The safety needle device as recited in claim 5, wherein the retraction spring is positioned between the actuator and the elongate housing.

7. The safety needle device as recited in claim 6, wherein the spring is positioned within a first chamber of the elongate member and the needle assembly is positioned in a second chamber of the elongate member.

8. The safety needle device as recited in claim 7, wherein the first and second chambers have parallel longitudinal axes which are offset from each other.

9. The safety needle device as recited in claim 8, wherein a first end of the spring is affixed to a spring mount of the actuator and a second end of the spring is affixed to the elongate housing.

10. The safety needle device as recited in claim 5, wherein the release button is movable between a first position engageable with the elongate housing and a second position disengaged from the elongate housing.

11. The safety needle device as recited in claim 5, wherein the needle assembly includes a needle and a tube extending proximally from the needle.

12. The safety needle device as recited in claim 11, wherein the actuator is affixed to the tube.

13. A method of preventing inadvertent retraction of a spring biased safety needle comprising:

providing a safety needle having an elongate housing including an upper chamber and a lower chamber, a needle assembly movably mounted from an advanced position to a retracted position located within the elongate housing and an actuator, wherein a release button is operatively disposed at a distal end of the actuator and a spring mount is operatively disposed at a proximal end of the actuator, each of the release button and spring mount is slidable within the upper chamber of the elongate housing, the release button movably mounted from a first position preventing movement of the needle assembly from the advanced position to the retracted position to a second position allowing movement of the needle assembly from the advanced position to the retracted position; and providing a removable blocking member on the safety needle in engagement with the release button of the actuator such that the blocking member prevents movement of the release button from the first position to the second position.

14. The method as recited in claim 13, wherein the step of providing a removable blocking member includes positioning a removable blocking member between the release button and the needle assembly.

15. The method as recited in claim 14, wherein the needle assembly includes a tube and the step of providing a removable blocking member includes positioning a removable blocking member between the release button and the tube.

16. The method as recited in claim 15, wherein the needle assembly further includes a needle extending distally from the tube and, the removable blocking member includes a surety sheath, wherein the step of providing a removable blocking member includes the step of inserting the safety sheath over the needle and between the tube and the release button.

* * * * *

UNITED STATES PATENT AND TRADEMARK OFFICE
CERTIFICATE OF CORRECTION

PATENT NO. : 7,611,486 B2  Page 1 of 1
APPLICATION NO. : 11/525377
DATED : November 3, 2009
INVENTOR(S) : Jones et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 412 days.

Signed and Sealed this

Twelfth Day of October, 2010

David J. Kappos
*Director of the United States Patent and Trademark Office*